US010580414B2

(12) United States Patent
Zhang et al.

(10) Patent No.: US 10,580,414 B2
(45) Date of Patent: Mar. 3, 2020

(54) SPEAKER RECOGNITION/LOCATION USING NEURAL NETWORK

(71) Applicant: Microsoft Technology Licensing, LLC, Redmond, WA (US)

(72) Inventors: Shixiong Zhang, Redmond, WA (US); Xiong Xiao, Bothell, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 16/006,405

(22) Filed: Jun. 12, 2018

(65) Prior Publication Data

US 2019/0341057 A1  Nov. 7, 2019

Related U.S. Application Data

(60) Provisional application No. 62/668,125, filed on May 7, 2018.

(51) Int. Cl.
*G10L 17/18* (2013.01)
*G01S 3/803* (2006.01)
*G10L 25/78* (2013.01)

(52) U.S. Cl.
CPC ............ *G10L 17/18* (2013.01); *G01S 3/8034* (2013.01); *G10L 25/78* (2013.01)

(58) Field of Classification Search
CPC ........ G10L 17/18; G10L 25/78; G01S 3/8034
USPC ....................................................... 704/232
See application file for complete search history.

(56) References Cited

U.S. PATENT DOCUMENTS

| 9,621,984 | B1* | 4/2017 | Chu | H04R 1/406 |
| 2010/0333163 | A1* | 12/2010 | Daly | H04N 5/4403 |
| | | | | 725/133 |
| 2015/0127336 | A1 | 5/2015 | Lei et al. | |
| 2017/0309292 | A1 | 10/2017 | Eddington, Jr. | |
| 2017/0351769 | A1* | 12/2017 | Karakas | G06Q 50/01 |

(Continued)

OTHER PUBLICATIONS

Youssef et al. Simultaneous Identification and Localization of Still and Mobile Speakers Based on Binaural Robot Audition 2016 13 pages.*

(Continued)

*Primary Examiner* — Quynh H Nguyen
(74) *Attorney, Agent, or Firm* — Alleman Hall Creasman & Tuttle LLP

(57) ABSTRACT

Computing devices and methods utilizing a joint speaker location/speaker identification neural network are provided. In one example a computing device receives a multi-channel audio signal of an utterance spoken by a user. Magnitude and phase information features are extracted from the signal and inputted into a joint speaker location/speaker identification neural network that is trained via utterances from a plurality of persons. A user embedding comprising speaker identification characteristics and location characteristics is received from the neural network and compared to a plurality of enrollment embeddings extracted from the plurality of utterances that are each associated with an identity of a corresponding person. Based at least on the comparisons, the user is matched to an identity of one of the persons, and the identity of the person is outputted.

20 Claims, 10 Drawing Sheets

(56) References Cited

U.S. PATENT DOCUMENTS

2018/0018970 A1* 1/2018 Heyl .................. G10L 17/18
2019/0043508 A1* 2/2019 Sak .................. G10L 17/005

OTHER PUBLICATIONS

Arslan, et al., "A Unified Neural-Network-Based Speaker Localization Technique", In the Journal of IEEE Transactions on Neural Networks Archive, vol. 11, Issue 4, Jul. 1, 2000, 6 Pages.
"International Search Report and Written Opinion Issued in PCT Application No. PCT/US2019/029768", dated Jul. 5, 2019, 12 Pages.

* cited by examiner

SPEAKER RECOGNITION/LOCATION USING NEURAL NETWORK

CROSS REFERENCE TO RELATED APPLICATIONS

This application claims priority to U.S. Provisional Patent Application Ser. No. 62/668,125, filed May 7, 2018, the entirety of which is hereby incorporated herein by reference for all purposes.

BACKGROUND

Speaker recognition technologies may include speaker identification (ID) systems that identify a person by analyzing characteristics of the person's voice. In some examples, sound source localization (SSL) systems also may be used to locate an active speaker. Both speaker ID systems and SSL systems may be used to achieve speaker diarization, or partitioning an audio stream of a multi-person conversation into homogeneous segments in which a single speaker is active in each segment.

SUMMARY

Various examples are disclosed herein that relate to utilizing a neural network for speaker recognition. For example, one disclosed example provides a computing device that utilizes a joint speaker location/speaker identification neural network that is trained using both magnitude features and phase information features from multi-channel audio signals. In runtime, the joint speaker location/speaker identification neural network may receive a multi-channel audio signal of a user's utterance, and may utilize both magnitude features and phase information features from the signal to generate a user embedding comprising speaker identification characteristics and location characteristics.

The user embedding may be compared to a plurality of enrollment embeddings extracted from utterances that are each associated with an identity of a corresponding person. Based at least on the comparisons, the user may be matched to an identity of one of the persons, and the identity of the person may be outputted and utilized for a variety of purposes and functions. In some examples, an angular orientation of the user also may be determined and outputted.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
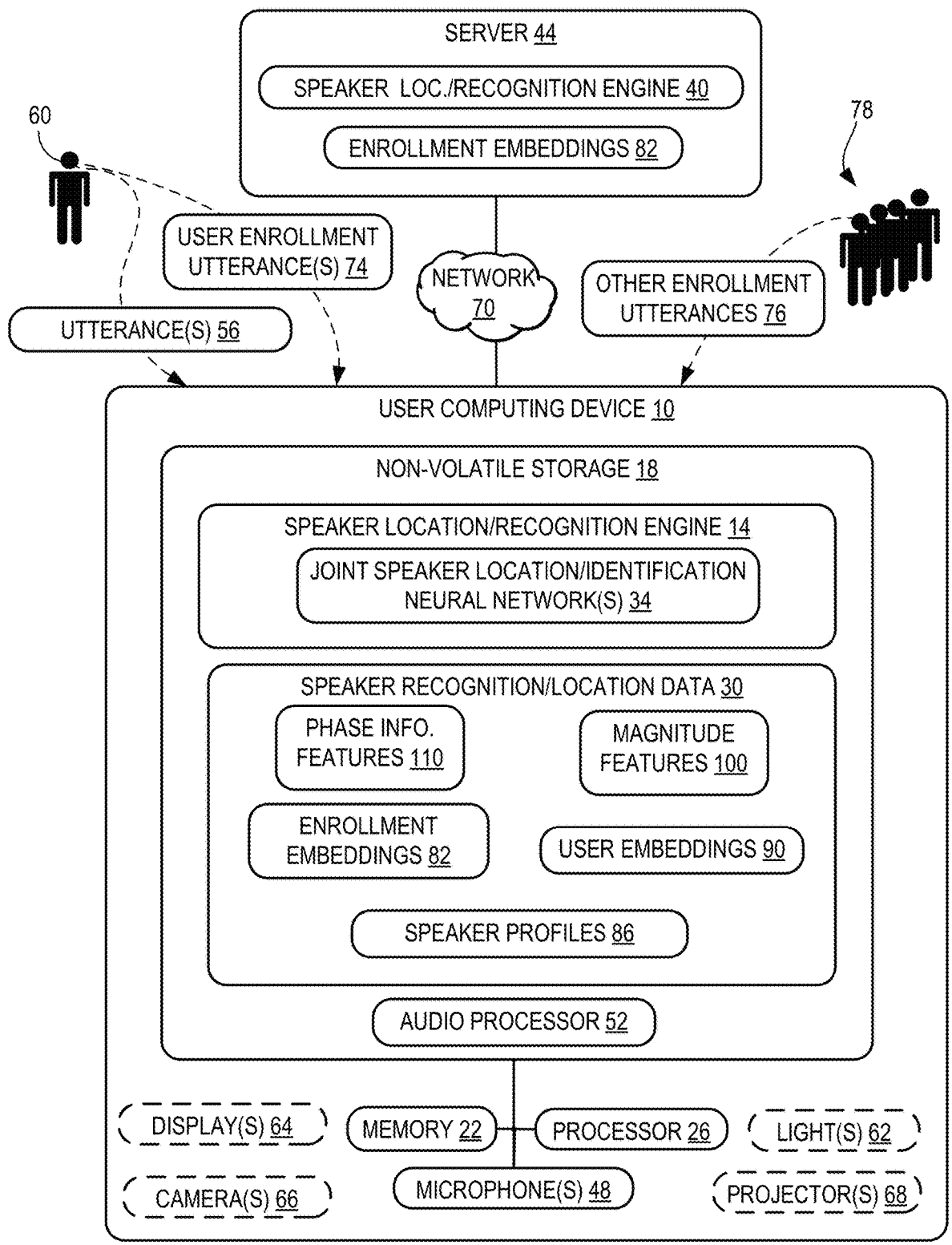
FIG. 1 is a schematic depiction of a user computing device for recognizing and locating a user's voice using a joint speaker location/speaker identification neural network according to examples of the present disclosure.

Speaker recognition and location systems may be utilized in a variety of applications. In some examples, speaker recognition may be used to identify a person who is speaking (e.g., speaker identification). Example applications include forensic investigations that may compare one or more sample utterances to candidate utterances from a set of enrollment speakers. In these examples, speaker recognition technologies may determine whether the sample utterance(s) matches a candidate utterance associated with a known identity. Speaker location technologies such as SSL may be used to locate an active speaker relative to one or more microphones in a physical environment, such as a living room or a meeting room.

In some situations, two or more people may engage in a conversation. In these scenarios, a speaker diarization system may determine who is speaking at any instance of the conversation or meeting. To achieve this, the system may partition an audio stream of a multi-person conversation into homogeneous segments in which a single speaker is active in each segment. Each individual speaking may then be identified based on characteristics found in that person's unique vocal qualities.

Both speaker ID and SSL systems have their limitations. For example, when two speakers have similar vocal characteristics, a speaker ID system may not be able to accurately determine the boundary of a speaker change or identify the different segments. On the other hand, when two speakers are sitting close to one another, an SSL system may not be able to determine the spatial position difference between the two speakers. Additionally, when a speaker ID system is trained with audio signal magnitude data, such as Log Mel filterbanks, it does not have access to spatial information of the speakers. Thus, the determinations made by the speaker ID system are made by using just the speaker characteristics information. Similarly, when an SSL system is trained with speaker spatial information, such as generalized cross correlation (GCC) and steered response power (SRP) features, it does not have access to the speaker's vocal characteristics.

As described in more detail below, examples of the present disclosure provide computing devices and methods that utilize a joint speaker location/speaker identification neural network to enhance both speaker ID and speaker location results. By training this joint model with both speaker vocal characteristics and speaker spatial information, the system is able to exploit both types of information to provide more accurate and useful speaker ID and location results. Additionally and as described in the use case examples provided below, advantages provided by the present disclosure may be utilized to enhance a variety of user devices and experiences, such as smart assistant devices, audio and video conferencing systems, audio-based monitoring systems, and various Internet of Things (IoT) devices.

Examples of performing speaker recognition and location with a user computing device that utilizes one or more joint speaker location/speaker identification neural networks will now be provided. As described in use case examples discussed below, magnitude features, such as Log Mel filterbanks, and phase information features, such as (GCC and SRP features, may be extracted from multi-channel audio signals comprising spoken utterances. These features are inputted into one or more joint speaker location/speaker identification neural networks. The joint speaker location/speaker identification neural network comprises a batch input layer and a deep architecture that processes the magnitude and phase information features through a plurality of layers to yield an output of a plurality of speaker features. In some examples, the joint speaker location/speaker identification neural network may comprise a feedforward network, such as a convolution neural network (CNN). In other examples, one or more other types or classes of artificial neural networks may be utilized with the present disclosure. For example, one or more recurrent neural networks (RNNs) may be utilized.

In one potential advantage of the present disclosure, the joint speaker location/speaker identification neural network is trained using both magnitude and phase information features from training and/or enrollment speech. Output from the joint speaker location/speaker identification neural network may be utilized by a speaker recognition program to perform speaker identification and/or determine speaker location in a variety of applications.

Turning now to FIG. 1, a schematic illustration of a user computing device 10 that includes a speaker recognition/location engine 14 according to examples of the present disclosure is provided. As explained in more detail below, one or more joint speaker location/speaker identification neural networks 34 may be trained and utilized by the speaker recognition/location engine 14 in performing speaker recognition tasks. The speaker recognition/location engine 14 may be stored in non-volatile storage 18 of the user computing device 10. The speaker recognition/location engine 14 may be loaded into memory 22 and executed by a processor 26 to perform one or more of the methods and processes described in more detail below.

The non-volatile storage 18 may include speaker recognition/location data 30 generated or received by the speaker recognition/location engine 14. In some examples, speaker recognition/location engine 14 may cooperate with one or more other speaker recognition programs, such as a speaker location/recognition engine 40 located on remote server 44, to perform one or more of the methods and processes described in more detail below.

As shown in the example of FIG. 1, the user computing device 10 may include or be communicatively coupled with one or more audio input devices, such as microphone array 48. In different examples, microphone array 48 may be integrated into user computing device 10 or may be located remotely from the client computing device and may communicate with the device via wired or wireless communication. Audio input from a user may be captured by the microphone array 48 and provided to an audio processor 52 for processing into audio data. For example, one or more utterances 56 from a user 60 may be captured by microphone array 48. In some examples, microphone array 48 may utilize 7 microphones. In other examples, any suitable number of microphones may be utilized.

In some examples, user computing device 10 may also include one or more additional input or output components. For example, different examples of a user computing device 10 may include one or more displays 64, infrared, color, stereoscopic, depth camera(s) 66, light indicators 62, and/or projector(s) 68.

In different examples the user computing device 10 may take a variety of forms. In some examples, user computing device 10 may take the form of a standalone device that may be placed in home or work environment. For example, the standalone device may comprise or be communicatively coupled with an intelligent personal assistant program, and may enable a user to interact with the assistant program via voice commands. For example, a user may control a music player application, interact with a personal assistant application, request information, and perform other actions by speaking commands to the standalone device. In other examples user computing device 10 may take the form of an audio or audio/visual conferencing device, a desktop computer, laptop computer, tablet computer, mobile computer, smartphone, set-top device, gaming console, stand-alone display, or any other type of suitable computing device. In some examples, user computing device 10 may be embedded or otherwise included with other devices, components, vehicles, buildings, or other objects to enable the collection and exchange of data among devices.

In some examples, the user computing device 10 may be operatively connected with one or more other computing devices using a wired connection, or may employ a wireless connection via WiFi, Bluetooth, or any other suitable wireless communication protocol. As shown in FIG. 1, such other computing devices may include a server computing device 44. For example, the user computing device 10 and server computing device 44 may be communicatively coupled via a network 70. The network 70 may take the form of a local area network (LAN), wide area network (WAN), wired network, wireless network, personal area network, or a combination thereof, and may include the Internet In some examples, user computing device 10 may offload speaker recognition and location tasks to another device having more robust capabilities by transferring speaker recognition and/or location data to the other device. In some use case examples, a user computing device may communicate with one or more cloud-based services on remote computing device(s) via a network. For example, user computing device 10 may not include the speaker location/recognition engine 14 and may offload speaker recognition/location tasks to server 44. Additional details regarding the components and computing aspects of the user computing device 10 and server computing devices 44 are described in more detail below with reference to FIG. 9.

Figure 2:
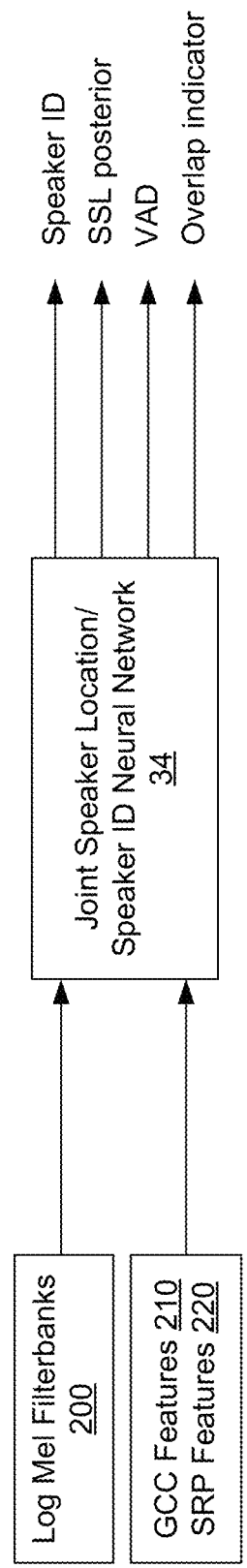
FIG. 2 is a schematic depiction of inputs into and outputs from a joint speaker location/speaker identification neural network according to examples of the present disclosure.
Figure 3:
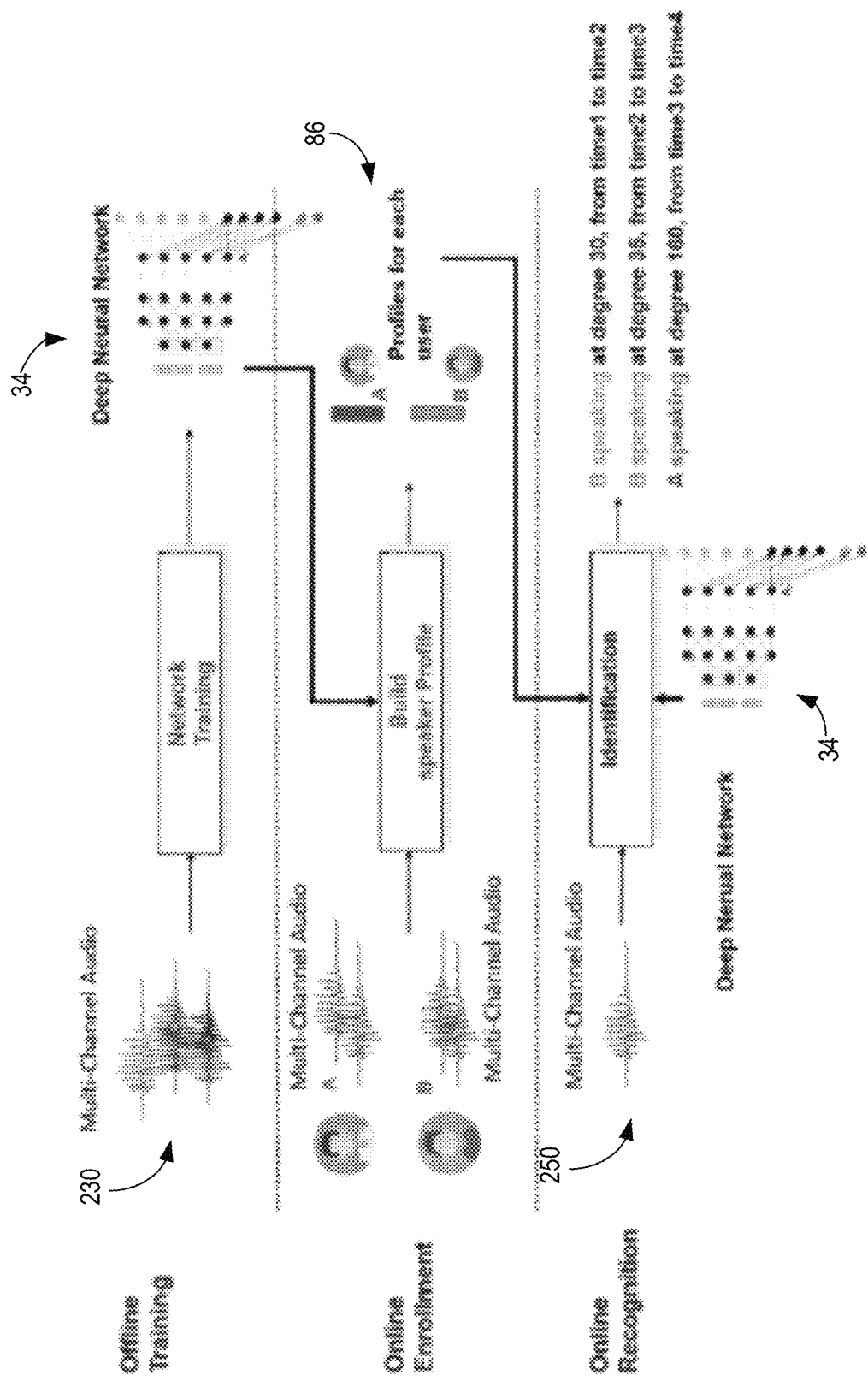
FIG. 3 is a schematic depiction of different phases of utilizing a joint speaker location/speaker identification neural network according to examples of the present disclosure.

As described in the use case examples below, the speaker location/recognition engine 14 may utilize output from the joint speaker location/speaker identification neural network 34 to perform various speaker recognition and location functions. With reference now to FIGS. 2 and 3, examples of joint speaker location/speaker identification neural network 34 are illustrated. As noted above, magnitude (amplitude) features 100 such as Log Mel filterbanks 200, and phase information features 110, such as GCC features 210 and SRP features 220, may be extracted from a multi-channel audio signal of a spoken utterance and inputted into the joint speaker location/speaker identification neural network 34.

Figure 4:
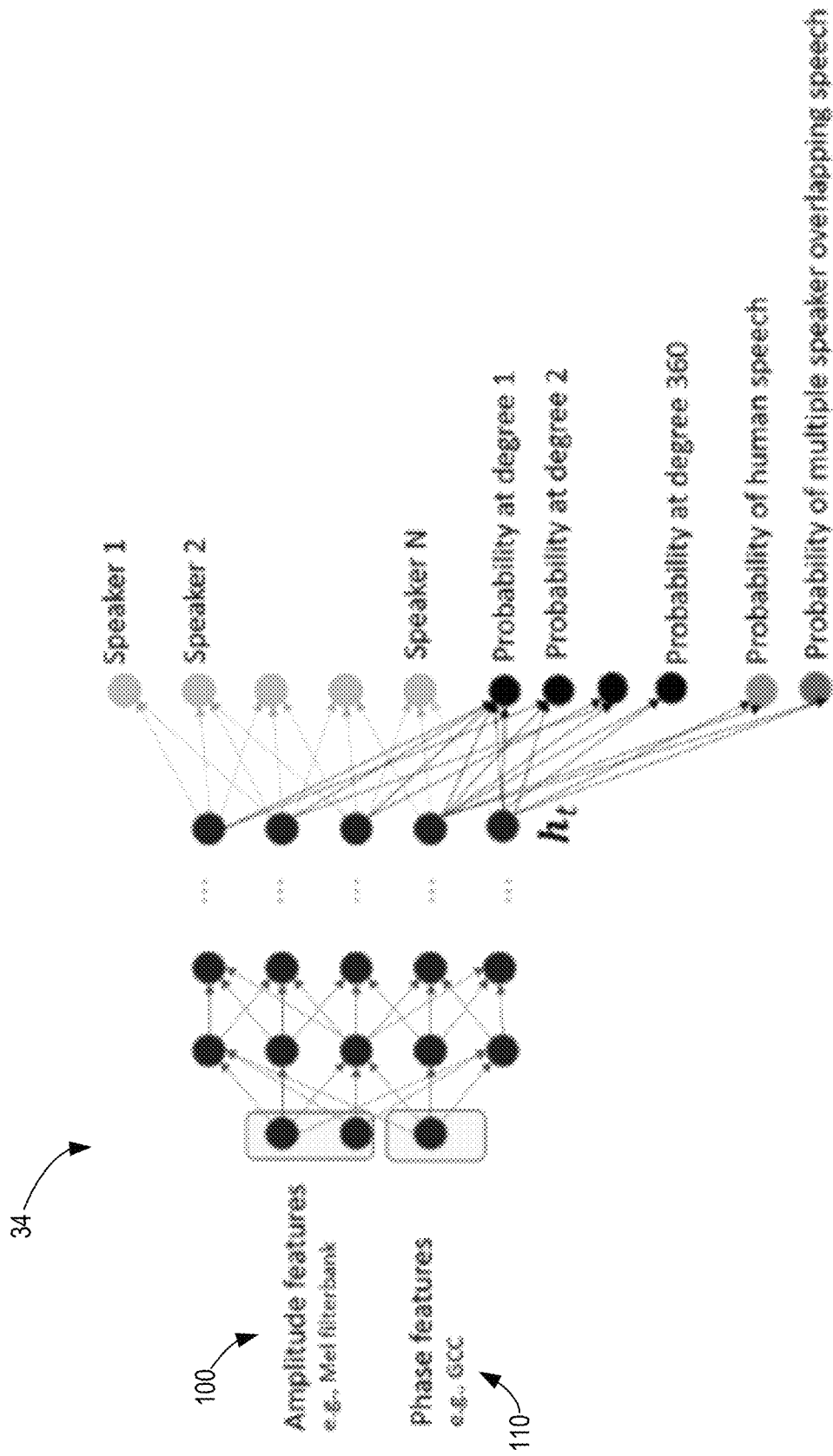
FIG. 4 is a simplified schematic illustration of a joint speaker location/speaker identification neural network according to examples of the present disclosure.

The magnitude features 100 and phase information features 110 may comprise multi-dimensional vectors. In one example, Log Mel filterbanks 200 may be represented by a 100 dimension vector, and the GCC features 210 also may be represented by a 100 dimension vector. These two multi-dimensional vectors may be combined to form a 200 dimension vector that is fed into the joint speaker location/speaker identification neural network 34. It will be appreciated that in other examples, many differently sized multi-dimensional vectors may be utilized. In different examples, feature selection and classification functions embedded in the joint speaker location/speaker identification neural network 34 may output vectors having a different number of dimensions. As illustrated in FIG. 4, the joint speaker location/speaker identification neural network 34 processes the magnitude features 100 and phase information features 110 through a plurality of layers to yield a plurality of speaker identification and location features described below.

With reference to FIG. 3, in an offline training phase multi-channel audio signals 230 and their extracted magnitude and phase information features may be utilized to jointly train the joint speaker location/speaker identification neural network 34. Any suitable techniques for training neural networks, such as using backpropagation and variations of the Delta Rule, may be utilized. As noted above, by training the neural network with both speaker vocal characteristics and speaker spatial information, the system is able to exploit both types of information to provide more accurate and useful speaker ID and location results.

Similarly, in an online enrollment phase training of the joint speaker location/speaker identification neural network 34 may continue, and one or more speaker profiles may be generated and progressively enhanced. With reference again to FIG. 1, in the enrollment phase the speaker recognition/location engine 14 may receive multi-channel audio signals of enrollment utterances spoken by users of the user computing device 10 and by other persons. Each of the enrollment utterances may comprise training magnitude features and training phase information features. In this example, user 60 initially may speak one or more user enrollment utterances 74 during an enrollment phase. In some examples, one or more predetermined words or phrases may be spoken by the user 60. In other examples, freeform utterances of any word or words of the user 60 may be received. Similarly, in some examples audio signals of other enrollment utterances 76 from one or more other persons 78 may be received by the user computing device 10.

For each enrollment utterance 74, 76, an identity of an enrollment person who spoke the corresponding enrollment utterance is associated with the utterance. For example, metadata of the enrollment person identity may be stored with an enrollment embedding 82 for each enrollment utterance. The enrollment utterances 74, 76 may be used to train the joint speaker location/speaker identification neural network 34 of the speaker recognition/location engine 14 as described above. In this manner, enrollment embeddings 82 that represent models of each person's voice and include location information relative to the device 10 may be generated. Such enrollment embeddings 82 may be stored locally on the user computing device 10. As described in more detail below, the enrollment embeddings 82 may be utilized to develop speaker profiles 86 for different users of the device.

With reference also to FIG. 3 and in a runtime or "online recognition" phase, multichannel audio signals 250 from user utterances 56 are processed by the joint speaker location/speaker identification neural network 34 to generate user embeddings 90 comprising speaker identification characteristics and speaker location characteristics. The user embeddings are compared to the enrollment embeddings 82 extracted from the enrollment utterances that are each associated with an identity of a corresponding enrollment person 60, 78. Based at least on the comparisons, the user is matched to an identity of one of the enrollment persons, and the identity of the user is outputted.

Figure 5:
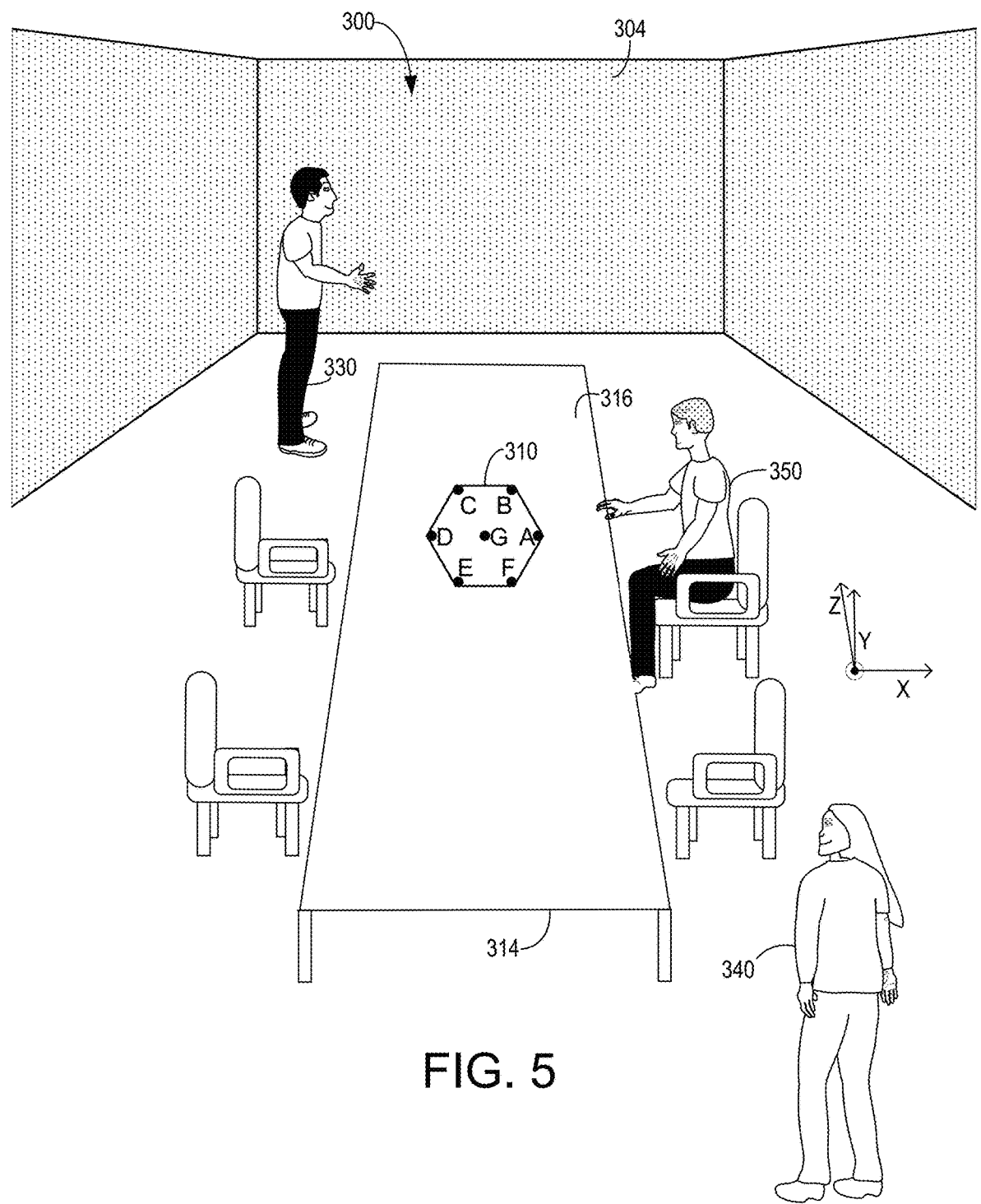
FIG. 5 is a schematic depiction of a room including a user computing device for recognizing and locating a user's voice according to examples of the present disclosure.

In some examples, the joint speaker location/speaker identification neural network 34 is configured to utilize location characteristics of the user embedding 90 to determine an angular orientation of the user with respect to a microphone array that captured the multi-channel audio signal of the utterance spoken by the user. With reference to FIG. 5, in one example three people may be in a meeting room 300 with a user computing device 10 in the form of an audio conferencing device 310 on a table 314 in the room. The audio conferencing device 310 includes a microphone array having 7 microphones A-G that capture and generate 7-channel audio data. Audio data received from the microphone array may be processed and analyzed by the joint speaker location/speaker identification neural network 34 to determine an estimated location of an active speaker in the room 300. In some examples, the audio data may be used to generate an SSL distribution corresponding to an estimated location of the active speaker with respect to the audio conferencing device 310. For example with reference also to FIG. 2, posterior probabilities of speech present at 1-360 degrees in the 2D plane of the room 300 may be generated and output.

In some examples, techniques based on time delay estimates (TDEs) may be utilized to generate an SSL distribution. TDEs utilize the principle that sound reaches the differently located microphones at slightly different times. The delays may be computed using, for example, cross-correlation functions between the signals from different microphones. In some examples, different weightings (such as maximum likelihood, PHAT, etc.) may be used to address reliability and stability of the results under noise and/or reverberation conditions. In this manner, GCC features 210 may be generated.

In a similar manner, one or more beamforming-based approaches such as SRP-PHAT algorithms may be utilized to generate SRP features 220 from the audio data.

In one example, an SSL distribution in an x-axis direction across the room 300 may be generated using audio data from the microphone array of audio conferencing device 310. The SSL distribution may comprise a probability distribution function (PDF) indicating a probability of an active speaker located along the PDF. In some examples, an estimated location of the active speaker along an azimuth that corresponds to a peak of the PDF may be determined. In some examples, the azimuth may be defined by a vector extending from the audio conferencing device 310 toward the peak of the SSL distribution, with the vector projected onto a reference plane parallel to the surface 316 of table 314. In this example, the azimuth is the angle between the projected vector and a reference vector extending in the z-axis direction in the reference plane perpendicular from the video conferencing device 310.

In some examples, such an estimated location may be used by the joint speaker location/speaker identification neural network 34 to estimate a location of the active speaker in room 300. In some examples, the joint speaker location/speaker identification neural network 34 may utilize the estimated location to output an angular orientation along with an identity of the enrollment person matched to the user. For example and with reference again to FIG. 4, for a given time t the joint speaker location/speaker identification neural network may output the probability that the speaker is located at a range of angles with respect to the audio conferencing device 310. In the present example, for each degree between 1-360 degrees around the audio conferencing device, the joint speaker location/speaker identification neural network may output a probability that the active speaker is located at each degree.

Figure 6:
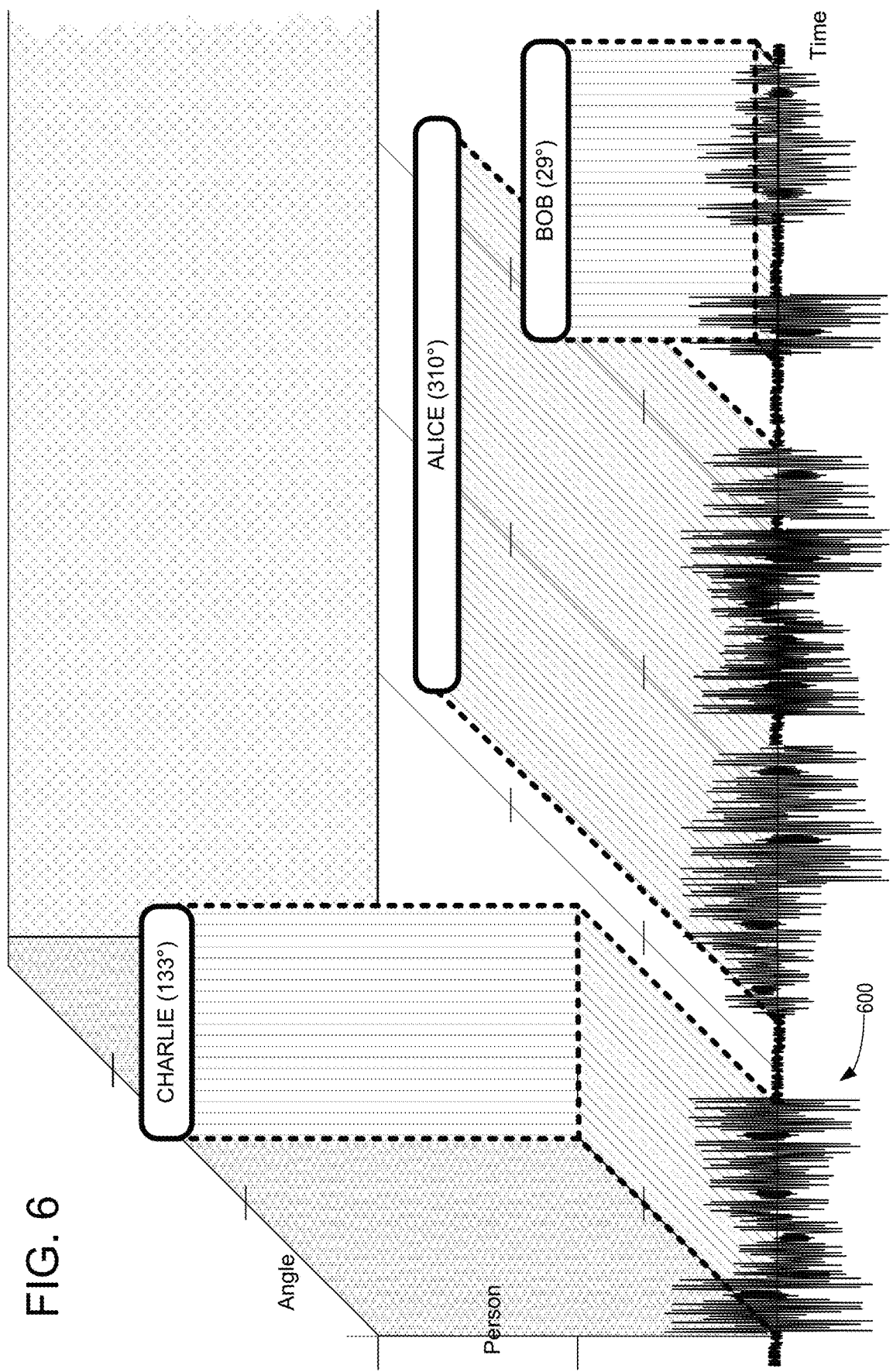
FIG. 6 is a schematic depiction of outputs from a joint speaker location/speaker identification neural network processing a conversation according to examples of the present disclosure

As noted above, by training the joint speaker location/speaker identification neural network 34 with both magnitude features 100 and phase information features 110, the network may exploit both types of information to provide more accurate and useful speaker identification and location results. In some examples, the joint speaker location/speaker identification neural network 34 may use magnitude features 100 of a spoken utterance to determine an angular orientation of the speaker with respect to a microphone array that captured the utterance spoken. With reference again to FIG. 5, in one example user Charlie 330 may be standing in one corner of room 300, user Alice 340 in the diagonally opposite corner, and user Bob 350 may sit at the table 314. With reference now to the example of FIG. 6, outputs from the joint speaker location/speaker identification neural network 34 may be utilized by the speaker location/recognition engine 14 to determine which user is speaking at a particular time along with the angular location of the speaker with respect to the audio conferencing device 310.

In this example, the multi-channel audio signal 600 is analyzed to determine that user Charlie 330 speaks for a period of time followed by a break, then Alice 340 speaks for a longer period of time followed by a break, and then Bob 350 speaks. As this conversation continues and each speaker remains at their respective angular locations, the joint speaker location/speaker identification neural network 34 learns to associate each speaker's identity with her or his angular location with respect to the audio conferencing device 310.

At one point in the conversation, background noise from an adjacent room behind the wall 304 may be heard as user Alice 340 begins speaking ½ second after user Bob spoke. The background noise may affect the phase information features 110 processed by the joint speaker location/speaker identification neural network 34, and may reduce the probability of isolating and locating Alice's voice to a particular angular location. For example, a PDF may have multiple peak values corresponding to locations near wall 304 and near user Alice 340.

In this example, the joint speaker location/speaker identification neural network 34 may utilize the magnitude features 100 of the current audio signal to identify the speaker as user Alice 340 with a relatively high degree of probability. Additionally, by also examining the recent conversation history and noting the consistent association between user Alice 340 and the angular location of 310 degrees, the joint speaker location/speaker identification neural network 34 may utilize the speaker ID (Alice) determined by the current magnitude features to also determine the angular orientation of Alice at 310 degrees. In this manner, the joint speaker location/speaker identification neural network 34 may improve the performance and accuracy of the speaker location/speaker recognition engine 14 and audio conferencing device 310 by utilizing the current magnitude features to determine Alice's location, even in situations where the phase information features alone may be insufficient to enable an accurate determination of her location. It follows that these additional capabilities provided by the joint speaker location/speaker identification neural network 34 also provide more pleasing and consistent user interactions and experiences with devices utilizing such network.

In some examples, the joint speaker location/speaker identification neural network 34 may utilize both the magnitude features 100 and the phase information features 110 in a collaborative fashion to determine the speaker's location. For example, where a PDF has multiple peak values, the joint speaker location/speaker identification neural network 34 determines a consistent association between user Alice 340 and the angular location of 310 degrees, and 310 degrees also corresponds to one of the peaks of the PDF, the joint speaker location/speaker identification neural network 34 may utilize all of this information to determine a high probability that user Alice 340 is located at 310 degrees. In this manner, and in another potential advantage of the present disclosure, the joint speaker location/speaker identification neural network 34 may improve the performance and accuracy of the speaker location/speaker recognition engine 14 and audio conferencing device 310 by utilizing both magnitude and phase information features collaboratively to determine Alice's location.

In a similar manner, in some examples the joint speaker location/speaker identification neural network 34 may utilize phase information features 110 to determine an identity of the user. At one point in the conversation above, other background noise is received by the audio conferencing device 310 as user Bob 350 begins speaking 1 second after user Charlie finishes speaking. This background noise may mix with Bob's voice to alter the magnitude features 100 processed by the joint speaker location/speaker identification neural network 34, and may significantly reduce the ability of the speaker location/recognition engine 14 to identify user Bob 350 as the current speaker.

In this example, the joint speaker location/speaker identification neural network 34 may utilize the phase information features 110 of the current audio signal to locate the source of the human speech at an angular orientation of 29 degrees with a relatively high degree of probability. Advantageously, by also examining the recent conversation history and noting the consistent association between user Bob 350 and the angular location of 29 degrees, the joint speaker location/speaker identification neural network 34 may utilize the angular orientation determined by the current phase information features to also determine the identity of the speaker as user Bob 350. In this manner, the joint speaker location/speaker identification neural network 34 utilizes both the magnitude features 100 and the phase information features 110 in a collaborative fashion to determine the speaker's identity. Accordingly and in this additional aspect, the joint speaker location/speaker identification neural network 34 enables the audio conferencing device 310 to provide more pleasing and consistent user interactions and experiences with devices utilizing such network.

In the above examples, the output of the current speaker's identity and location relative to the microphone array receiving the audio may be utilized in a variety of manners with a variety of different user computing devices. For example, a smart assistant device utilizing a joint speaker location/ speaker identification neural network 34 as described herein may be configured to recognize a spoken keyword or key phrase and determine the identity and location of the person speaking the keyword or phrase with respect to the device. Upon recognition of the keyword, the smart assistant device may be configured to activate one or more functions, such as more robust speech recognition functionality. The smart assistant device also may be configured to refrain from activating these functions when human speech is received that is not preceded by the keyword.

In some examples, a joint speaker location/speaker identification neural network 34 as described herein may be utilized to enable one or more exceptions to the device's keyword recognition rules that provide more natural and user-friendly experiences with the device. For example, the device may utilize the joint speaker location/speaker identification neural network 34 to identify and locate a first user who speaks the keyword followed by a request to the device. After this first utterance, a follow-up utterance may be received that does not begin with the keyword. As described above, the joint speaker location/speaker identification neural network 34 may identify the first user as the speaker of the follow-up utterance. Based at least on identifying the first user as the speaker, and despite not receiving the keyword, the device may activate the one or more functions normally associated with receipt of the keyword. Advantageously, in this manner the joint speaker location/speaker identification neural network 34 may enable the smart assistant device to provide more natural and user-friendly interactions and assistance to users.

The device also may determine that the location of the first user when speaking the follow-up utterance has not changed from the first user's location speaking the first utterance. In some examples, the device may activate the one or more functions normally associated with receipt of the keyword also based on determining that the location of the first user has not changed.

Figure 7:
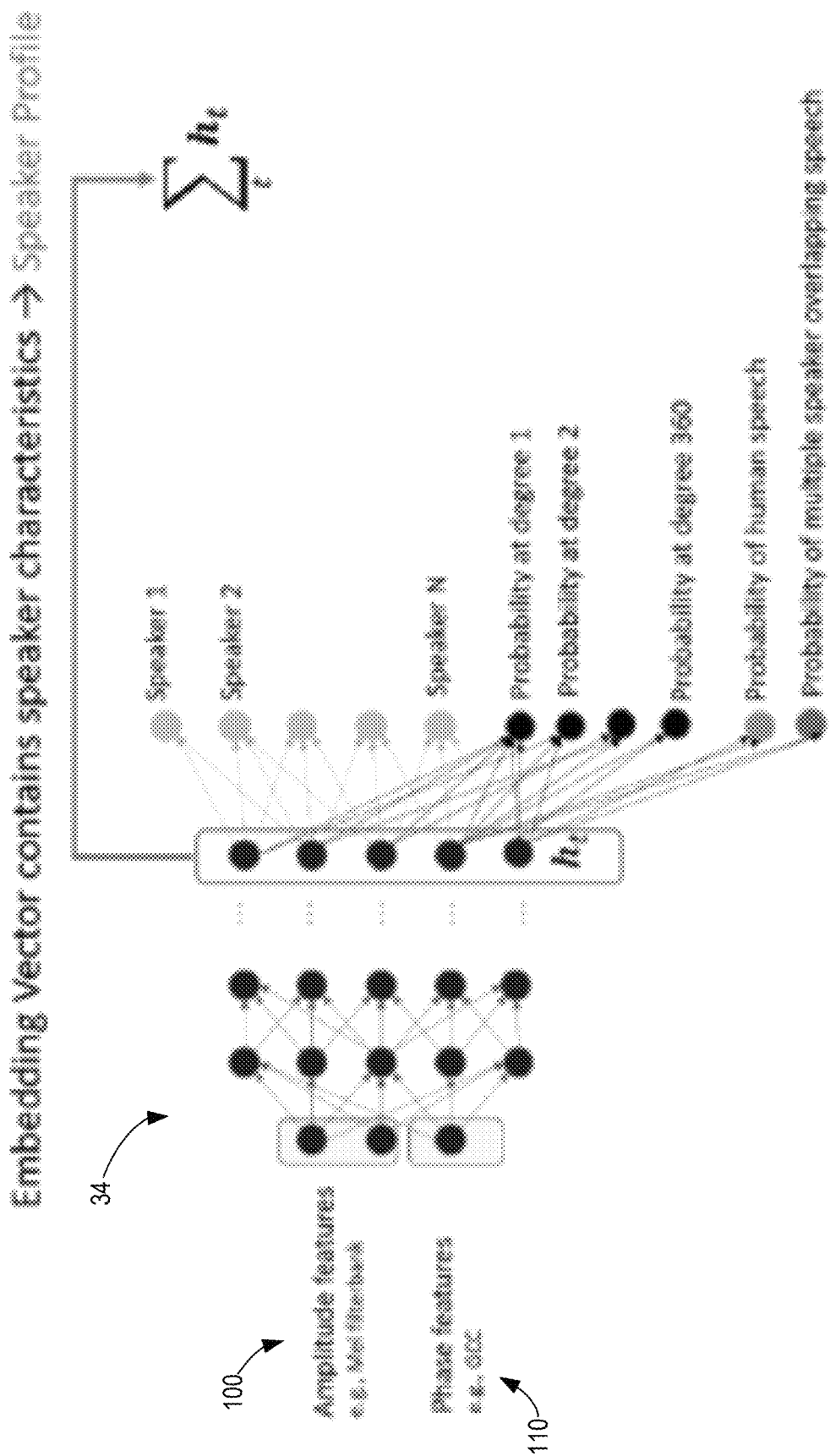
FIG. 7 is a schematic depiction of updating a speaker profile using a joint speaker location/speaker identification neural network according to examples of the present disclosure.

With reference now to FIG. 7, in some examples the joint speaker location/speaker identification neural network 34 may be configured to utilize user embeddings to enhance a speaker profile of the user. In some examples, for each time t that a user is speaking, a speaker characteristics vector_t will contain location information. While a speaker profile 86 is being constructed, the speaker location/speaker identification neural network 34 may be configured to average out the location information associated with the received audio. For example, during enrollment a speaker may speak enrollment utterances at different positions relative to the receiving microphone array. By combining/averaging these vector_t characteristics, a more complete voiceprint of the speaker may be generated independent of where the speaker is speaking. Alternatively expressed, the generated vector distills all the information (voiceprint and location), and the joint speaker location/speaker identification neural network 34 selects relevant information to make speaker identification and location predictions.

With reference again to FIGS. 2 and 7, the joint speaker location/speaker identification neural network 34 also may determine voice activity detection (VAD) characteristics from a multi-channel audio signal. In some examples, where a user embedding further comprises VAD characteristics, the speaker location/recognition engine 14 may determine if the VAD characteristics indicate a human voice. Where the VAD characteristics do not indicate a human voice, then the speaker location/recognition engine 14 may refrain from utilizing this user embedding to enhance a speaker profile. In a similar manner, determining that the VAD characteristics do not indicate a human voice also may be utilized to manage a variety of other functionalities of different user computing devices.

Similarly, the joint speaker location/speaker identification neural network 34 also may determine voice overlap (Overlap) characteristics from a multi-channel audio signal. In some examples, where a user embedding comprises Overlap characteristics, the joint speaker location/speaker identification neural network 34 may determine if the Overlap characteristics indicate that the audio data contains two or more people speaking at the same time. Where the Overlap characteristics indicate that two or more voices are overlapping, then the joint speaker location/recognition engine 14 may refrain from utilizing this user embedding to enhance a speaker profile. In a similar manner, determining that the Overlap characteristics indicate that multiple voices are overlapping also may be utilized to manage a variety of other functionalities of different user computing devices.

In some use case examples, different user computing devices 10 may utilize one or more features of the joint speaker location/recognition engine 14 to record and generate transcriptions of conversations between multiple people. For example, in a classroom setting a user computing device 10 may identify the teacher and different students to generate a written transcription of a class discussion that includes notations indicating the identity of the speaker of each portion of dialogue.

In some examples, aspects of the joint speaker location/recognition engine 14 described herein may be utilized by user computing devices 10 to track and follow a changing location of a speaker. For example, a user computing device 10 in the form of a smart assistant device may include a moveable camera or display that may be directed toward a location of the person speaking. Using location information generated by the joint speaker location/recognition engine 14, the camera and/or display may follow the user as her location relative to the device changes.

In some use cases where just the location of the speaker (and not the identity of the speaker) is tracked, information from the speaker's profile may not be needed. For example, where the joint speaker location/recognition engine 14 knows at time t–1 that sound is received from an angle of 10 degrees, and at time t the system detects a continuous sound from an angle of 11 degrees, and these two sounds are from the same person (determined by comparing the characteristics vector_t), then the system can determine that both sounds are from the same speaker, and thereby track this speaker.

In some examples of a conversation between multiple speakers, the joint speaker location/speaker identification neural network 34 described herein may be utilized to detect if there is a change in the person speaking without utilizing enrollment information. For example, in a meeting with multiple participants an audio conferencing device may receive an audio signal of the conversation containing utterances from multiple speakers. In this situation, the joint speaker location/speaker identification neural network 34 may continuously analyze the signal and utilize both magnitude features 100 and phase information features 110 to detect changes in speaker vocal characteristics and changes in location of the current speaker. Using this information, and without utilizing any pre-enrolled audio data from these speakers, the joint speaker location/speaker identification neural network 34 may determine when there is a change in the person speaking. For example, the joint speaker location/speaker identification neural network 34 may determine a boundary between a first utterance from a first speaker and a second utterance from a second speaker without utilizing information from the enrollment utterances.

Figure 8A:
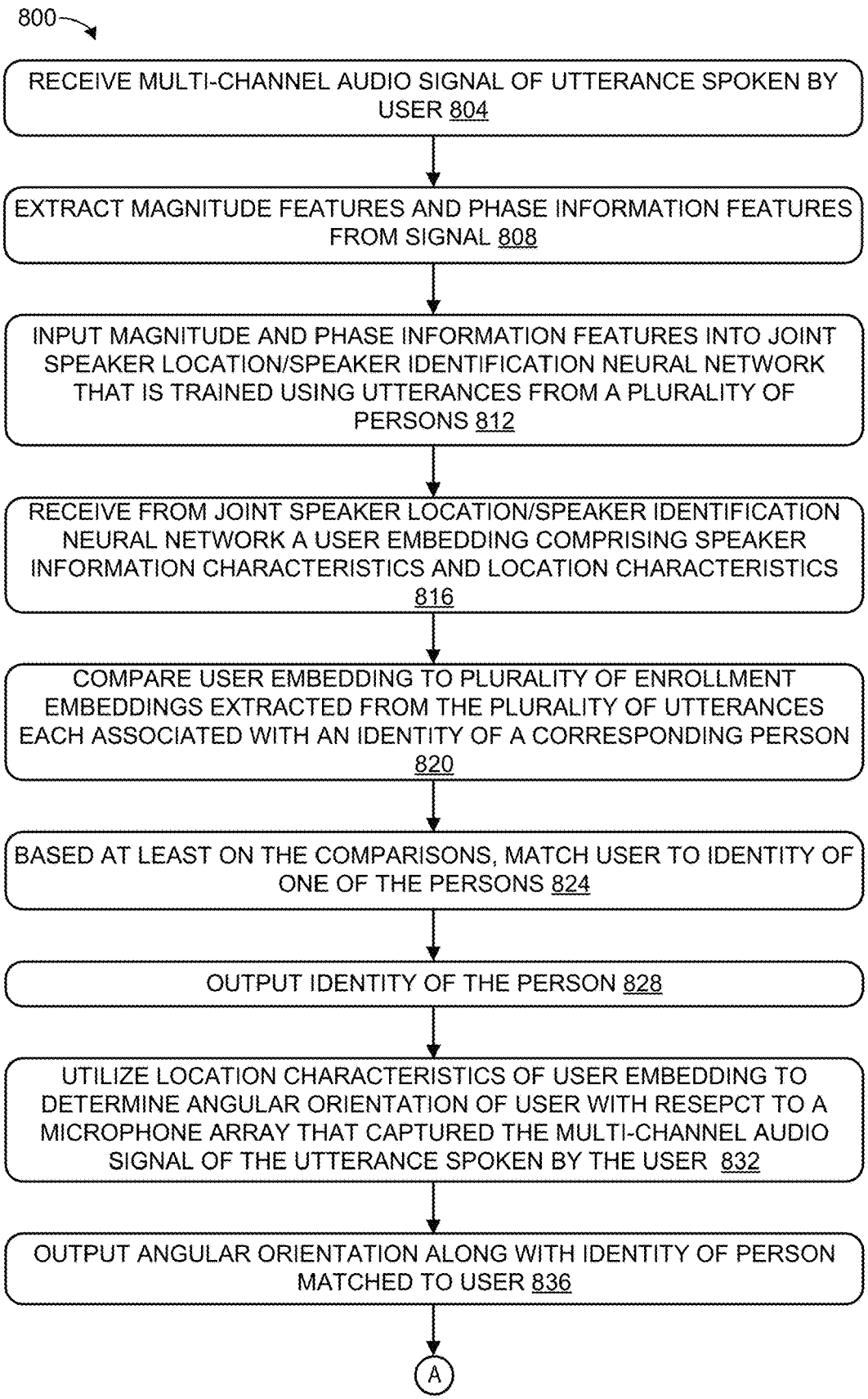
FIGS. 8A and 8B show a flow diagram illustrating an example method of using a joint speaker location/speaker identification neural network according to examples of the present disclosure.
Figure 8B:
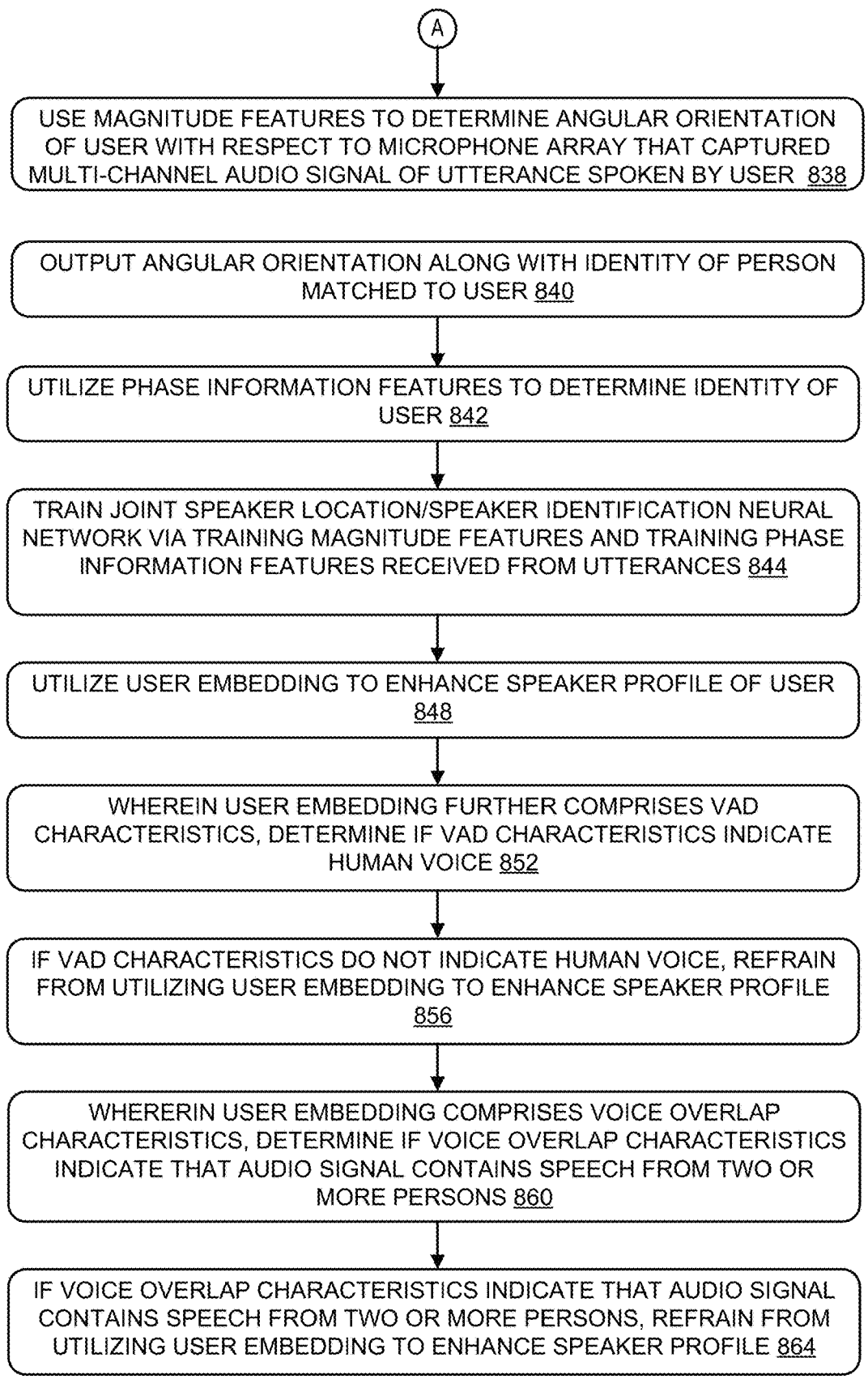

FIGS. 8A and 8B illustrate an example method 800 for using a joint speaker location/speaker identification neural network according to examples of the present disclosure. In some examples method 800 may be performed by user computing device 10 and/or audio conferencing device 310. The following description of method 800 is provided with reference to the software and hardware components described herein and shown in FIGS. 1-7 and 9. It will be appreciated that method 800 also may be performed in other contexts using other suitable hardware and software components.

With reference to FIG. 8A, at 804 the method 800 may include receiving a multi-channel audio signal of an utterance spoken by a user. At 808 the method 800 may include extracting magnitude features and phase information features from the signal. At 812 the method 800 may include inputting the magnitude features and the phase information features into a joint speaker location/speaker identification neural network, wherein the joint speaker location/speaker identification neural network is trained using a plurality of utterances from a plurality of persons. At 816 the method 800 may include receiving from the joint speaker location/speaker identification neural network a user embedding comprising speaker identification characteristics and location characteristics.

At 820 the method 800 may include comparing the user embedding to a plurality of enrollment embethlings extracted from the plurality of utterances that are each associated with an identity of a corresponding person. At 824 the method 800 may include, based at least on the comparisons, matching the user to an identity of one of the persons. At 828 the method 800 may include outputting the identity of the person. At 832 the method 800 may include utilizing the location characteristics of the user embedding to determine an angular orientation of the user with respect to a microphone array that captured the multi-channel audio signal of the utterance spoken by the user. At 836 the method 800 may include outputting the angular orientation along with the identity of the person matched to the user.

With reference now to FIG. 8B, at 838 the method 800 may include using the magnitude features to determine an angular orientation of the user with respect to a microphone array that captured the multi-channel audio signal of the utterance spoken by the user. At 840 the method 800 may include outputting the angular orientation along with the identity of the person matched to the user. At 842 the method 800 may include utilizing the phase information features to determine the identity of the user. At 844 the method 800 may include training the joint speaker location/speaker identification neural network via training magnitude features and training phase information features received from the utterances.

At 848 the method 800 may include utilizing the user embedding to enhance a speaker profile of the user. At 852 the method 800 may include, wherein the user embedding further comprises voice activity detection (VAD) characteristics, determining if the VAD characteristics indicate a human voice. At 856 the method 800 may include, if the VAD characteristics do not indicate a human voice, then refraining from utilizing the user embedding to enhance the speaker profile. At 860 the method 800 may include, wherein the user embedding comprises voice overlap characteristics, determining if the voice overlap characteristics indicate that the audio signal contains speech from two or more persons. At 864 the method 800 may include, if the voice overlap characteristics indicate that the audio signal contains speech from two or more persons, then refraining from utilizing the user embedding to enhance the speaker profile.

It will be appreciated that method 800 is provided by way of example and is not meant to be limiting. Therefore, it is to be understood that method 800 may include additional and/or alternative steps relative to those illustrated in FIGS. 8A and 8B. Further, it is to be understood that method 800 may be performed in any suitable order. Further still, it is to be understood that one or more steps may be omitted from method 800 without departing from the scope of this disclosure.

In some embodiments, the methods and processes described herein may be tied to a computing system of one or more computing devices. In particular, such methods and processes may be implemented as a computer-application program or service, an application-programming interface (API), a library, and/or other computer-program product.

Figure 9:
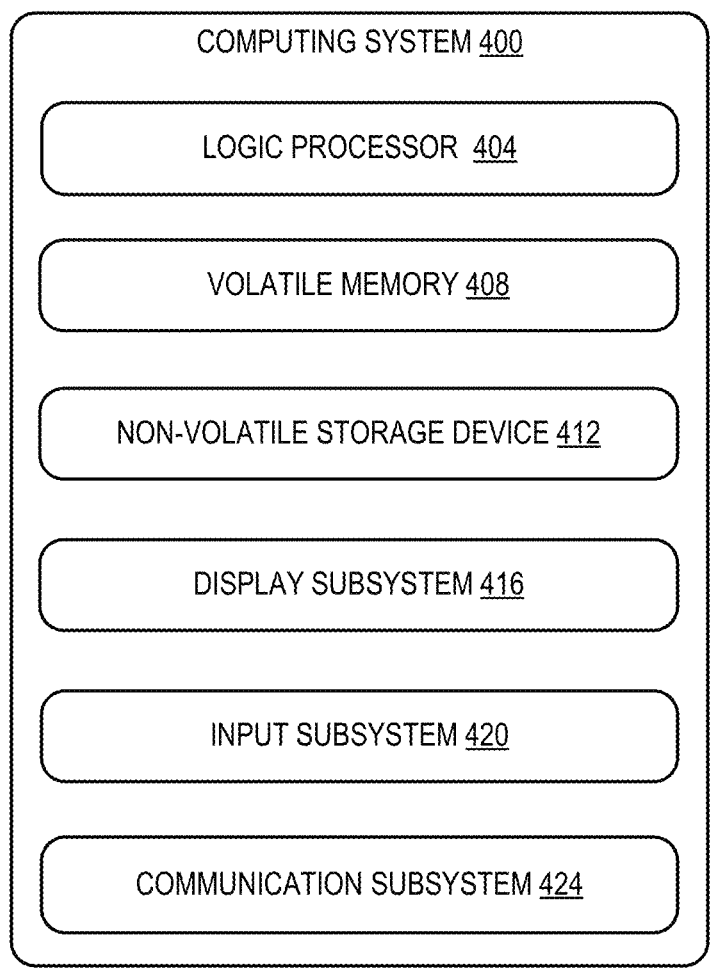
FIG. 9 is a schematic depiction of an example computing system according to examples of the present disclosure.

FIG. 9 schematically shows a non-limiting embodiment of a computing system 400 that can enact one or more of the methods and processes described above. Computing system 400 is shown in simplified form. User computing device 10, audio conferencing device 310, and server computing device 44 may take the form of computing system 400.

Computing system 400 includes a logic processor 404, volatile memory 408, and a non-volatile storage device 412. Computing system 400 may optionally include a display subsystem 416, input subsystem 420, communication subsystem 424, and/or other components not shown in FIG. 9.

Logic processor 404 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 404 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 404 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 404 may be virtualized and executed by remotely accessible, networked computing devices configured in a cloud-computing configuration. In such a case, these virtualized aspects may be run on different physical logic processors of various different machines.

Volatile memory 408 may include physical devices that include random access memory. Volatile memory 408 is typically utilized by logic processor 404 to temporarily store information during processing of software instructions. It will be appreciated that volatile memory 408 typically does not continue to store instructions when power is cut to the volatile memory.

Non-volatile storage device 412 includes one or more physical devices configured to hold instructions executable by the logic processors to implement the methods and processes described herein. When such methods and processes are implemented, the state of non-volatile storage device 412 may be transformed—e.g., to hold different data.

Non-volatile storage device 412 may include physical devices that are removable and/or built-in. Non-volatile storage device 412 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 412 may include nonvolatile, dynamic, static, read/write, read-only, sequential-access, location-addressable, file-addressable, and/or content-addressable devices. It will be appreciated that non-volatile storage device 412 is configured to hold instructions even when power is cut to the non-volatile storage device.

Aspects of logic processor 404, volatile memory 408, and non-volatile storage device 412 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "program" and "engine" may be used to describe an aspect of computing system 400 implemented to perform a particular function. In some cases, a program or engine may be instantiated via logic processor 404 executing instructions held by non-volatile storage device 412, using portions of volatile memory 408. It will be understood that different programs or engines may be instantiated from the same application, service, code block, object, library, routine, API, function, etc. Likewise, the same program or engine may be instantiated by different applications, services, code blocks, objects, routines, APIs, functions, etc. The terms "program" and "engine" encompasses individual or groups of executable files, data files, libraries, drivers, scripts, database records, etc.

When included, display subsystem 416 may be used to present a visual representation of data held by non-volatile storage device 412. As the herein described methods and processes change the data held by the non-volatile storage device, and thus transform the state of the non-volatile storage device, the state of display subsystem 416 may likewise be transformed to visually represent changes in the underlying data. Display subsystem 416 may include one or more display devices utilizing virtually any type of technology. Such display devices may be combined with logic processor 404, volatile memory 408, and/or non-volatile storage device 412 in a shared enclosure, or such display devices may be peripheral display devices.

When included, input subsystem 420 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include one or more microphones for speech and/or voice recognition, such as microphone array 48; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; and/or any other suitable sensor.

When included, communication subsystem 424 may be configured to communicatively couple computing system 400 with one or more other computing devices. Communication subsystem 424 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 400 to send and/or receive messages to and/or from other devices via a network such as the Internet.

The following paragraphs provide additional support for the claims of the subject application. One aspect provides, a computing device, comprising: a processor; and a memory holding instructions executable by the processor to: receive a multi-channel audio signal of an utterance spoken by a user; extract magnitude features and phase information features from the signal; input the magnitude features and the phase information features into a joint speaker location/speaker identification neural network, wherein the joint speaker location/speaker identification neural network is trained using a plurality of utterances from a plurality of persons; receive from the joint speaker location/speaker identification neural network a user embedding comprising speaker identification characteristics and location characteristics; compare the user embedding to a plurality of enrollment embeddings extracted from the plurality of utterances that are each associated with an identity of a corresponding person; based at least on the comparisons, match the user to an identity of one of the persons; and output the identity of the person. The computing device may additionally or alternatively include, wherein the joint speaker location/speaker identification neural network is configured to utilize the location characteristics of the user embedding to determine an angular orientation of the user with respect to a microphone array that captured the multi-channel audio signal of the utterance spoken by the user, and the instructions are executable to output the angular orientation along with the identity of the person matched to the user. The computing device may additionally or alternatively include, wherein the joint speaker location/speaker identification neural network is configured to use the magnitude features to determine an angular orientation of the user with respect to a microphone array that captured the multi-channel audio signal of the utterance spoken by the user; and the instructions are executable to output the angular orientation along with the identity of the person matched to the user. The computing device may additionally or alternatively include, wherein the joint speaker location/speaker identification neural network utilizes the phase information features to determine the identity of the user. The computing device may additionally or alternatively include, wherein the joint speaker location/speaker identification neural network is trained via training magnitude features and training phase information features received from the utterances. The computing device may additionally or alternatively include, wherein the joint speaker location/speaker identification neural network is configured to utilize the user embedding to enhance a speaker profile of the user. The computing device may additionally or alternatively include, wherein the user embedding further comprises voice activity detection (VAD) characteristics, and the instructions are executable to: determine if the VAD characteristics indicate a human voice; and if the VAD characteristics do not indicate a human voice, then refrain from utilizing the user embedding to enhance the speaker profile. The computing device may additionally or alternatively include, wherein the user embedding comprises voice overlap characteristics, and the instructions are executable to: determine if the voice overlap characteristics indicate that the audio signal contains speech from two or more persons; and if the voice overlap characteristics indicate that the audio signal contains speech from two or more persons, then refrain from utilizing the user embedding to enhance the speaker profile. The computing device may additionally or alternatively include, wherein the computing device is standalone device comprising a microphone array, and the microphone array captures the multi-channel audio signal of the utterance. The computing device may additionally or alternatively include, wherein the computing device receives the multi-channel audio signal of the utterance from a remote device comprising a microphone that captures the audio signal. The computing device may additionally or alternatively include, wherein the user is a first user and the utterance is a first utterance, the multi-channel audio signal further comprises a second utterance spoken by a second user, and the instructions are executable to determine a boundary between the first utterance and the second utterance without utilizing information from the plurality of utterances used to train the joint speaker location/speaker identification neural network.

Another aspect provides, at a computing device, a method comprising: receiving a multi-channel audio signal of an utterance spoken by a user; extracting magnitude features and phase information features from the signal; inputting the magnitude features and the phase information features into a joint speaker location/speaker identification neural network, wherein the joint speaker location/speaker identification neural network is trained via utterances from a plurality of persons; receiving from the joint speaker location/speaker identification neural network a user embedding comprising speaker identification characteristics and location characteristics; comparing the user embedding to a plurality of enrollment embeddings extracted from the plurality of utterances that are each associated with an identity of a corresponding person; based at least on the comparisons, matching the user to an identity of one of the persons; and outputting the identity of the person. The method may additionally or alternatively include utilizing the location characteristics of the user embedding to determine an angular orientation of the user with respect to a microphone array that captured the multi-channel audio signal of the utterance spoken by the user; and outputting the angular orientation along with the identity of the person matched to the user. The method may additionally or alternatively include using the magnitude features to determine an angular orientation of the user with respect to a microphone array that captured the multi-channel audio signal of the utterance spoken by the user; and outputting the angular orientation along with the identity of the person matched to the user. The method may additionally or alternatively include utilizing the phase information features to determine the identity of the user. The method may additionally or alternatively include training the joint speaker location/speaker identification neural network via training magnitude features and training phase information features received from the utterances. The method may additionally or alternatively include utilizing the user embedding to enhance a speaker profile of the user. The method may additionally or alternatively include, wherein the user embedding further comprises voice activity detection (VAD) characteristics, determining if the VAD characteristics indicate a human voice; and if the VAD characteristics do not indicate a human voice, then refraining from utilizing the user embedding to enhance the speaker profile. The method may additionally or alternatively include, wherein the user embedding comprises voice overlap characteristics, determining if the voice overlap characteristics indicate that the audio signal contains speech from two or more persons; and if the voice overlap characteristics indicate that the audio signal contains speech from two or more persons, then refraining from utilizing the user embedding to enhance the speaker profile.

Another aspect provides a computing device, comprising: a processor; and a memory holding instructions executable by the processor to: receive a multi-channel audio signal of an utterance spoken by a user; extract magnitude features and phase information features from the signal; input the magnitude features and the phase information features into a joint speaker location/speaker identification neural network, wherein the joint speaker location/speaker identification neural network is trained using a plurality of utterances from a plurality of persons; receive from the joint speaker location/speaker identification neural network a user embedding comprising speaker identification characteristics and location characteristics; compare the user embedding to a plurality of enrollment embeddings extracted from the plurality of utterances that are each associated with an identity of a corresponding person; based at least on the comparisons, match the user to an identity of one of the persons; output the identity of the person; use the magnitude features to determine an angular orientation of the user with respect to a microphone array that captured the multi-channel audio signal of the utterance spoken by the user; and output the angular orientation of the user.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:
1. A computing device, comprising:
a processor; and
a memory holding instructions executable by the processor to:
receive a multi-channel audio signal of an utterance spoken by a user;
extract magnitude features and phase information features from the signal;
input the magnitude features and the phase information features into a joint speaker location and speaker identification neural network, wherein the joint speaker location and speaker identification neural network is trained using a plurality of utterances from a plurality of persons, wherein each utterance of the plurality of utterances comprises both speaker vocal characteristics and speaker spatial information that are used to train the joint speaker location and speaker identification neural network;

receive from the joint speaker location and speaker identification neural network a user embedding comprising speaker identification characteristics and location characteristics;

compare the user embedding to a plurality of enrollment embeddings extracted from the plurality of utterances that are each associated with an identity of a corresponding person;

based at least on the comparisons, match the user to an identity of one of the persons; and output the identity of the person.

2. The computing device of claim 1, wherein the joint speaker location and speaker identification neural network is configured to utilize the location characteristics of the user embedding to determine an angular orientation of the user with respect to a microphone array that captured the multi-channel audio signal of the utterance spoken by the user, and the instructions are executable to output the angular orientation along with the identity of the person matched to the user.

3. The computing device of claim 1, wherein the joint speaker location and speaker identification neural network is configured to use the magnitude features to determine an angular orientation of the user with respect to a microphone array that captured the multi-channel audio signal of the utterance spoken by the user; and the instructions are executable to output the angular orientation along with the identity of the person matched to the user.

4. The computing device of claim 1, wherein the joint speaker location and speaker identification neural network utilizes the phase information features to determine the identity of the user.

5. The computing device of claim 1, wherein the joint speaker location and speaker identification neural network is trained via training magnitude features and training phase information features received from the utterances.

6. The computing device of claim 1, wherein the joint speaker location and speaker identification neural network is configured to utilize the user embedding to enhance a speaker profile of the user.

7. The computing device of claim 6, wherein the user embedding further comprises voice activity detection (VAD) characteristics, and the instructions are executable to:

determine if the VAD characteristics indicate a human voice; and if the VAD characteristics do not indicate a human voice, then refrain from utilizing the user embedding to enhance the speaker profile.

8. The computing device of claim 6, wherein the user embedding comprises voice overlap characteristics, and the instructions are executable to:

determine if the voice overlap characteristics indicate that the audio signal contains speech from two or more persons; and if the voice overlap characteristics indicate that the audio signal contains speech from two or more persons, then refrain from utilizing the user embedding to enhance the speaker profile.

9. The computing device of claim 1, wherein the computing device is a standalone device comprising a microphone array, and the microphone array captures the multi-channel audio signal of the utterance.

10. The computing device of claim 1, wherein the computing device receives the multi-channel audio signal of the utterance from a remote device comprising a microphone that captures the audio signal.

11. The computing device of claim 1, wherein the user is a first user and the utterance is a first utterance, the multi-channel audio signal further comprises a second utterance spoken by a second user, and the instructions are executable to determine a boundary between the first utterance and the second utterance without utilizing information from the plurality of utterances used to train the joint speaker location and speaker identification neural network.

12. At a computing device, a method comprising:

receiving a multi-channel audio signal of an utterance spoken by a user;

extracting magnitude features and phase information features from the signal;

inputting the magnitude features and the phase information features into a joint speaker location and speaker identification neural network, wherein the joint speaker location and speaker identification neural network is trained using a plurality of utterances from a plurality of persons, wherein each utterance of the plurality of utterances comprises both speaker vocal characteristics and speaker spatial information that are used to train the joint speaker location and speaker identification neural network;

receiving from the joint speaker location and speaker identification neural network a user embedding comprising speaker identification characteristics and location characteristics;

comparing the user embedding to a plurality of enrollment embeddings extracted from the plurality of utterances that are each associated with an identity of a corresponding person;

based at least on the comparisons, matching the user to an identity of one of the persons; and outputting the identity of the person.

13. The method of claim 12, further comprising:

utilizing the location characteristics of the user embedding to determine an angular orientation of the user with respect to a microphone array that captured the multi-channel audio signal of the utterance spoken by the user; and outputting the angular orientation along with the identity of the person matched to the user.

14. The method of claim 12, further comprising:

using the magnitude features to determine an angular orientation of the user with respect to a microphone array that captured the multi-channel audio signal of the utterance spoken by the user; and outputting the angular orientation along with the identity of the person matched to the user.

15. The method of claim 12, further comprising utilizing the phase information features to determine the identity of the user.

16. The method of claim 12, further comprising training the joint speaker location and speaker identification neural network via training magnitude features and training phase information features received from the utterances.

17. The method of claim 12, further comprising utilizing the user embedding to enhance a speaker profile of the user.

18. The method of claim 17, wherein the user embedding further comprises voice activity detection (VAD) characteristics, the method further comprising:

determining if the VAD characteristics indicate a human voice; and if the VAD characteristics do not indicate a human voice, then refraining from utilizing the user embedding to enhance the speaker profile.

19. The method of claim 17, wherein the user embedding comprises voice overlap characteristics, the method further comprising:
- determining if the voice overlap characteristics indicate that the audio signal contains speech from two or more persons; and
- if the voice overlap characteristics indicate that the audio signal contains speech from two or more persons, then refraining from utilizing the user embedding to enhance the speaker profile.

20. A computing device, comprising:
- a processor; and
- a memory holding instructions executable by the processor to:
  - receive a multi-channel audio signal of an utterance spoken by a user;
  - extract magnitude features and phase information features from the signal;
  - input the magnitude features and the phase information features into a joint speaker location and speaker identification neural network, wherein the joint speaker location and speaker identification neural network is trained using a plurality of utterances from a plurality of persons, wherein each utterance of the plurality of utterances comprises both speaker vocal characteristics and speaker spatial information that are used to train the joint speaker location and speaker identification neural network;
  - receive from the joint speaker location and speaker identification neural network a user embedding comprising speaker identification characteristics and location characteristics;
  - compare the user embedding to a plurality of enrollment embeddings extracted from the plurality of utterances that are each associated with an identity of a corresponding person;
  - based at least on the comparisons, match the user to an identity of one of the persons;
  - output the identity of the person;
  - use the magnitude features to determine an angular orientation of the user with respect to a microphone array that captured the multi-channel audio signal of the utterance spoken by the user; and
  - output the angular orientation of the user.

* * * * *